May 4, 1965 H. W. MOTZKAU Plant Pat. 2,503
AZALEA PLANT
Filed Sept. 5, 1963
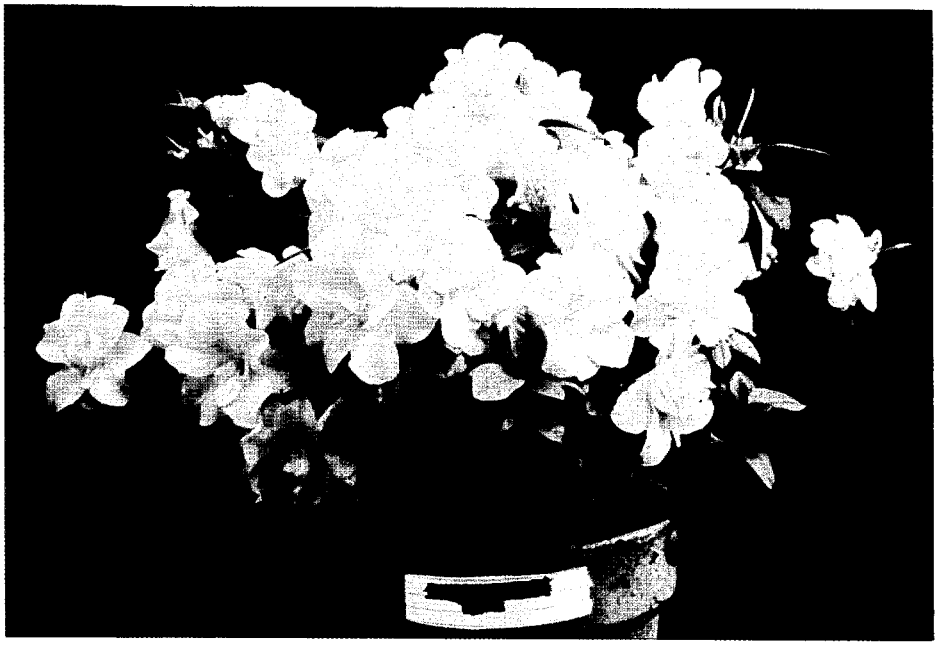
INVENTOR
H. W. MOTZKAU
By Robb & Robb
attorneys United States Patent Office Plant Pat. 2,503
Patented May 4, 1965

2,503
AZALEA PLANT

Henry W. Motzkau, Whitewater, Wis., assignor to Yoder Brothers, Inc., Barberton, Ohio, a corporation of Ohio Filed Sept. 5, 1963, Ser. No. 306,968
1 Claim. (Cl. Plt.—56)

My present invention relates to a new and distinct variety of azalea plant which has resulted from crossing certain varieties involved in a program of hybridization, the varieties not having any names but being designated as #525 and #302 for my purposes and in order to distinguish from others in the same program.

The object of the present invention has been to produce a new variety of azalea plant which will be as showy as the *Azalea indica* but not be faced with the production problems of said indica because of the slowness or relative slowness of its growth.

I have endeavored to and actually been able to take advantage of the vigor of the faster kurumes, in the instant invention, which in the program of hybridization availed of certain kurumes but not specific ones in the instant case which can be recalled or referred to, the purpose of the hybridization of the respective types being to obtain the advantages of both with some of the disadvantages of the same obviated hereby.

One of the particular advantages from the program and availing of the kurumes and in contrast to the kurumes is that the flower produced is substantially larger than that type, reaching under many circumstances a maximum diameter of three inches.

As heretofore pointed out, the program mentioned has involved the selection and crossing of nameless seedlings which in turn were the results of crossing and intercrossing the several types from which azaleas in general may be developed, the instant variety having been selected at least in this aspect because of its color, and the double flowers that do not drop from the plant when the blooming period is ended, keeping their substance at least 50% longer than the indica in general.

While the natural blooming period of the instant variety of azalea plant is from early mid-season, it can be flowered the year around with the aid of growth inhibitors and under refrigeration.

As a result of the specific hybridization previously mentioned, my new and distinct variety of azalea plant has shown more rapid vigorous growth with larger sized and double form of blooms, the longer lastingness and strong purplish pink color of its blooms being essential and important by way of distinction.

In point of fact the large size of the foliage is distinctive, being larger than is usually found on azalea plants.

More specifically, the blooms of my new variety are of a Strong Purplish Pink color (Nikerson Color Fan published by The Munsell Color Company) and as grown in the vicinity of Whitewater, Wisconsin, under uniform culture, plants of this variety have grown to a height in a year of about 6 inches, and 10 to 12 inches at the end of two years with a spread of 8 inches in one year and approximately 12 inches at the end of two years.

My new variety is a good keeper, with the blooming period depending upon the temperatures as indicated.

My new variety when grown in the region of Whitewater, Wisconsin is vigorous with large size foliage in abundant quantity, the normal weather conditions not being such as to adversely affect the growth or bloom, the blooms retaining their color to the end of the third week approximately.

My new variety has been asexually reproduced by cuttings of tips or sections of branches in the vicinity of Whitewater, Wisconsin and said new variety has been found to retain its distinctive characteristics through successive asexual reproduction.

The accompanying drawing forming a part hereof shows a typical plant of my new variety of azalea.

The following is a detailed description of my new variety of azalea plant, the color references being to the Nickerson Color Fan published by the Munsell Color Company:

*Description*

Parentage: Seedlings #525 and #302 (unpatented, my own hybridization).

Classification: Botanic—*Rhododendron hybrida.*

*Flower*

Blooming habit: From early mid-season and profusely. Observations were made in the vicinity of Whitewater, Wisconsin during February in the greenhouse.

Bud:
- *Size.*—Medium.
- *Form.*—Pointed.
- Bud not affected by wet or hot weather unless excessively so or for a continuous period.

Color:
- *When sepals first divide.*—7.5RP 6/12 Deep Purplish Pink.
- *When petals begin to unfurl.*—7.5RP 7/10 Strong Purplish Pink.
- *When half blown.*—7.5RP 7/10 Strong Purplish Pink.
- *Sepals.*—Smooth edge, drop as bud opens.
- *Peduncle.* — Length — short. Aspect — smooth. Strength—stiff. Bud opens well.

Bloom:
- *Size.*—Large.
- *Average size when fully expanded.*—About 2¾".
- *Borne.*—Several together.
- *Stems.*—Short, normal.
- *Form.*—When first open—cupped. Permanence—retains its form to the end.
- *Petalage.*—Double, hose-in-hose. Number of petals under normal conditions—15 or more.
- *Color.*—Center of flower—7.5RP 7/10 Strong Purplish Pink. Outer petals—7.5RP 7/10 Strong Purplish Pink. Base of petals—7.5RP 7/10 Strong Purplish Pink or faintly darker. Inside of petals—7.5RP 7/10 Strong Purplish Pink. Reverse of petals—7.5RP 7/10 Strong Purplish Pink. General tonality from a distance—7.5RP 7/10 Strong Purplish Pink.
- *Discoloration.*—Retains its color to the end of the third week at least.

Petals:
- *Texture.*—Soft; not adversely affected by hot or wet weather unless excessively hot or wet.
- *Appearance.*—Inside—satiny. Outside—satiny.
- *Form.*—Scalloped.
- *Arrangement.*—Informal.
- *Petaloids in center.*—Few and small.
- *Persistence.*—Hang on and dry.
- *Fragrance.*—None.
- *Lastingness.*—On the plant—long. As cut flower—fair.

Genital organs:
- *Stamens, anthers.*—Rare.
- *Styles.*—Columnar, even and of medium length.
- *Stigmas.*—7.5YR 9/4 Pale Orange Yellow.

Fruit: Variety is sterile with its own pollen.

Plant:
- *Form.*—Bush.
- *Growth.*—Vigorous, branching and compact.
- *Height.*—Approximate measurements of average plant—6″ one year, 10 to 12″ in two years. Spread—8″ in one year, 12″ in two years.

Foliage:

*Leaflets.*—Single.

*Size.*—Large for an azalea. Length—2½ inches average. Width—1⅜ inches average. Petiole—about ⅜ inch.

*Quantity.*—Abundant.

*Color.*—Upper side—7.5GY 5/7 Moderate Yellow Green. Under side—7.5 GY 6/8 Strong Yellow Green.

*Shape.*—Oval and oval pointed.

*Texture.*—Upper side—glossy and smooth.

*Ribs and veins.*—Light; impressed.

*Edge.*—Smooth.

Wood (new):

*Color.*—5GY 7/10 Strong Yellow Green.

*Bark.*—Smooth.

Wood (old):

*Color.*—2.5YR 6/12 Strong Orange.

*Bark.*—Smooth.

I claim:

A new and distinct variety of azalea plant substantially as herein disclosed, characterized as to novelty by its more rapid, vigorous growth, the larger size and double form of its blooms, the longer lastingness and the Strong Purplish Pink color of its blooms, the large size of its foliage, and the midseason, profuse and continuous flowering.

No references cited.

ABRAHAM G. STONE, *Primary Examiner.*